United States Patent [19]

Ryu et al.

[11] Patent Number: 5,489,687

[45] Date of Patent: Feb. 6, 1996

[54] HERBICIDAL QUINOLINYLOXADIAZOLES

[75] Inventors: Eung K. Ryu; Kun H. Chung, both of Daejeon; Won H. Lee, Chungchongnam-do; Jae N. Kim; Kyung S. Hong, both of Daejeon, all of Rep. of Korea

[73] Assignee: Korea Research Institute of Chemical Technology, Rep. of Korea

[21] Appl. No.: 381,870

[22] Filed: Feb. 13, 1995

[30] Foreign Application Priority Data

Aug. 14, 1992 [KR] Rep. of Korea ................. 1992-14704

[51] Int. Cl.$^6$ ................. C07D 413/14; C07D 413/04; A01N 43/836
[52] U.S. Cl. ............................. 546/167; 504/274
[58] Field of Search ................ 546/167; 504/274

[56] References Cited

U.S. PATENT DOCUMENTS

| | | | |
|---|---|---|---|
| 4,522,646 | 7/1985 | Markert et al. | 71/94 |
| 4,797,148 | 1/1989 | Hagen et al. | 71/94 |

FOREIGN PATENT DOCUMENTS

| | | |
|---|---|---|
| 104389 | 8/1983 | European Pat. Off. . |
| 3639837 | 6/1988 | Germany . |
| 3703113 | 8/1988 | Germany . |

OTHER PUBLICATIONS

Chem Abstracts, vol. 112, Nol. 17, Issued 1990 Apr. 23 (Columbus, Ohio) Zhang, Ziyi et al. "Synthesis of 2-aryl-5-(2-phenyl-4-quinolyl)-1,3,4-oxadiazole derivatives and related properties", p. 710, col. 1, Abstract No. 158 150Q, Youji Huaxue 1989, 9(4), 355-61 (CH).

*Primary Examiner*—David B. Springer
*Attorney, Agent, or Firm*—Finnegan, Henderson, Farabow, Garrett & Dunner

[57] ABSTRACT

The present invention relates to novel quinolinyloxadiazole derivatives of the following formula (I) having processes for their preparation and their use as herbicides and plant growth regulants, especially their use in the selective kill and control of barnyardgrass in the presence of rice.

wherein,

A and B are selected from the group consisting of hydrogen, halogen and $C_1$–$C_3$ lower alkyl;

R is a $C_3$–$C_4$ alkyl or cycloalkyl, phenyl, pyridyl, benzyl, phenoxyalkyl or phenylthioalkyl, and aromatic groups in these radicals are optionally substituted with 1–3 substituents selected from the group consisting of halogen, $C_1$–$C_4$ alkyl, $C_1$–$C_4$ alkoxy, $C_1$–$C_4$ alkylthio $C_2$–$C_6$ alkoxyalkyl and an anolog thereof.

13 Claims, No Drawings

HERBICIDAL QUINOLINYLOXADIAZOLES

BACKGROUND OF THE INVENTION

1. Field of the Invention

The present invention relates to novel quinolinyloxadiazoles of the following formula (I), their processes for the preparation, herbicidal compositions and the use of said compounds as herbicides and plant growth regulants.

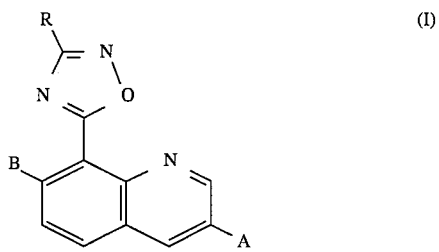

2. Description of the Related Art

The use of certain quinolinecarboxylic acid derivaties as herbicides is known in the art. For example, in the Af Chem New Product Review-Volume VIII, 1990; W. L. Hopkins Author, William L. Hopkins AG Chem Information Services, U.S.A. describes two quinolinecarboxylic acids known commercially as Quinclorac and Quinmerac. Quinclorac of the following formula(C) and Quinmerac have been disclosed in Ger. Offen. DE 3,639,837 and Ger Offen. DE 3,703,113.

Besides its activity on several weed species, Quinclorac possess a specific effectiveness against Echinochloa species.

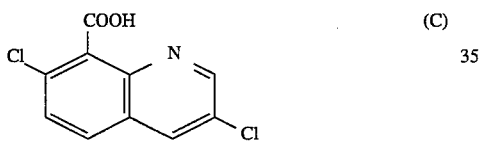

But, inventors of the present invention have discovered that certain novel quinolinyloxadiazole derivatives are highly active and more selective herbicides or plant growth regulants which are particularly useful for selective control of barnyardgrass species in upland and paddy rice with greater safety.

The object of the present invention is to provide compounds which are useful as herbicides, particularly those for use in paddy fields and herbicides containing the said compounds as active ingredients.

SUMMARY OF THE INVENTION

The novel compounds of the present invention are represented by the following formula (I).

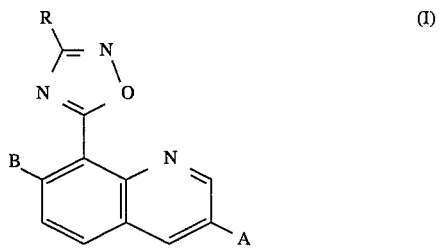

wherein,

A and B am selected from the group consisting of hydrogen, halogen and $C_1$–$C_4$ lower alkyl;

R is $C_3$–$C_4$ alkyl, $C_3$–$C_6$ cycloalkyl, phenyl, benzyl, phenoxyalkyl, phenylthioalkyl, pyridyl, thienyl or furanyl.

And where R is aromatic ring optionally substituted with substituents of 1~3 numbers or without substituent which is selected from the group consisting of halogen, nitro, a lower alkyl, a lower alkoxy and a lower haloalkyl. The herbicides of the present invention comprise a compound of the above formula (I) as their active ingredient.

DETAILED DESCRIPTION OF THE INVENTION

The present invention relates to quinolinyloxadiazole derivatives corresponding to the following formula (I)

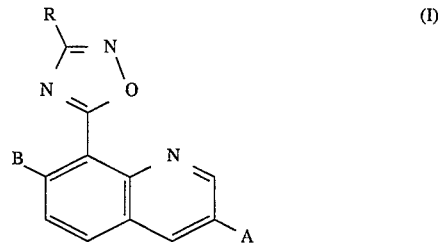

wherein,

A and B are selected from the group consisting of hydrogen, halogen and $C_1$–$C_4$ lower alkyl;

R is $C_3$–$C_4$ alkyl, $C_3$–$C_6$ cycloalkyl, phenyl, benzyl, phenoxyalkyl, phenylthioalkyl, pyridyl, thienyl or furanyl; And where phenyl and benzyl are optionally substituted with substituents of 1~3 numbers selected from the group consisting of halogen, $C_1$–$C_4$ alkyl, $C_1$–$C_4$ alkoxy, $C_1$–$C_4$ alkylthio, $C_1$–$C_4$ haloalkyl, $C_2$–$C_6$ alkoxyalkyl, nitro, hydroxy and methylenedioxy; phenoxyalkyl wherein the aromatic ring of said substituents may be optionally substituted with 1~3 substituents selected from the group consisting of halogen, $C_1$–$C_4$ alkyl, $C_1$–$C_4$ alkoxy, $C_1$–$C_4$ alkylthio, $C_1C_4$ haloalkyl, $C_2$–$C_6$ alkoxyalkyl, nitro, hydroxy and methylenedioxy; phenoxyalkyl wherein the alkyl group of said substituents may be $C_1$–$C_4$ alkyl; phenylthioalkyl wherein the aromatic ring of said substituents may be optionally substituted with 1~3 substituents selected from the group consisting of halogen, $C_1$–$C_4$ alkyl, $C_1$–$C_4$ alkoxy, $C_1$–$C_4$ alkylthio, $C_1$–$C_4$ haloalkyl, $C_2$–$C_6$ alkoxyalkyl, nitro, hydroxy and methylendioxy; phenythioalkyl wherein the alkyl group of said substituents may be $C_1$–$C_4$ alkyl; pyridyl, thienyl and furanyl wherein the heterocyclic ring may be optionally substituted with 1~3 substituents selected from the group consisting of halogen, $C_1$–$C_4$ alkyl, $C_1$–$C_4$ alkoxy, $C_1$–$C_4$ alkylthio, $C_1$–$C_4$ haloalkyl and $C_2$–$C_6$ alkoxyalkyl.

Preferred group of compounds of the above formula (I) is as follows:

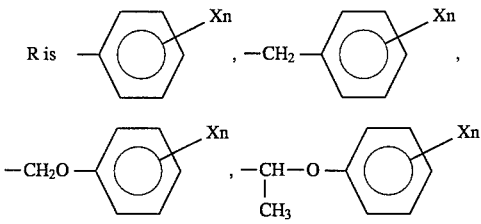

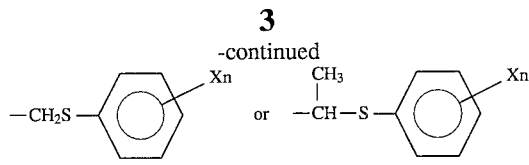

wherein X is $C_1$–$C_4$ alkyl or $C_1$–$C_4$ alkoxy chloro, fluoro, trifluoromethyl or nitro and n is 1~3.

Typical compounds of the formula (I) according to the present invention are:

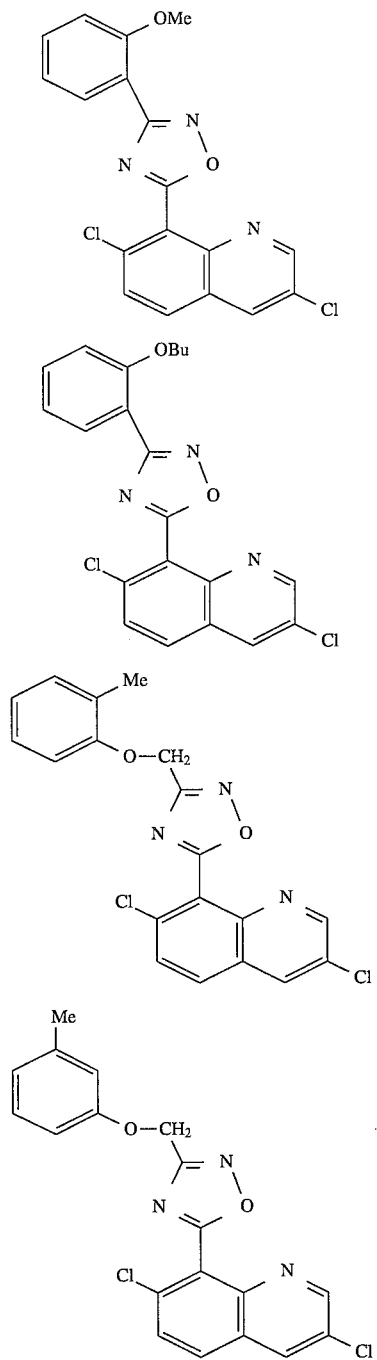

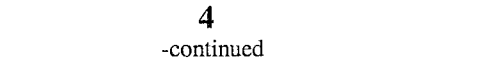

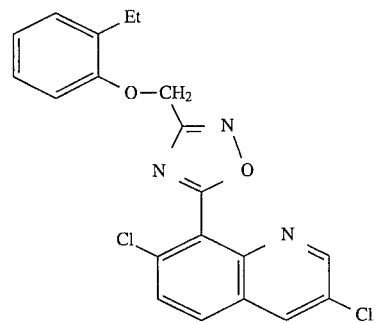

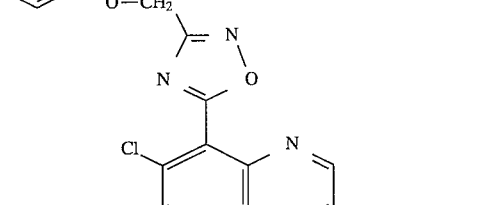

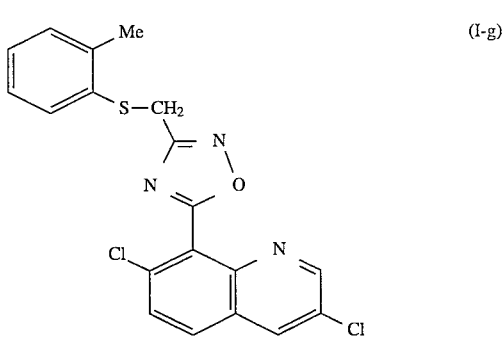

In the present invention, the typical compounds of the above formula (I) have highly herbicidal efficacy with better safety on rice and better selectivity between rice and barnyardgrass.

The compounds of the formula (I) according to the present invention may be prepared by the preparation process as the following reaction Scheme A.

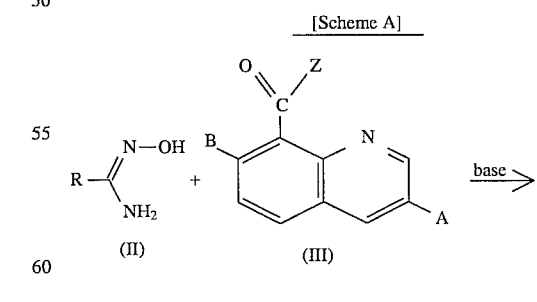

-continued
[Scheme A]

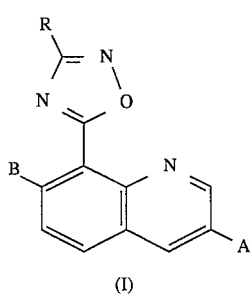

wherein,

R, A and B are respectively defined as the above formula (I),

Z is selected from the group consisting of a chloro, bromo, iodo, cyano, acetoxy and $C_1$–$C_4$ alkoxy group.

In the above Scheme A, the amidoximes of the above formula(II) are prepared from the nitrile compounds with hydroxylamine hydrochloride in a water-alcohol mixture in the presence of base. The carboxylic acid chloride(Z=Cl) of the above formula(III) is prepared from 3,7-dichloro-8-quinolinecarboxylic acid of the above formula(C) which is described on European Patent No. 104,389 with thionyl chloride.

The target compounds of the above formula (I) are prepared from the above compounds(II) and the above compound(III) in the presence of a base.

In preparing of the above formula (I), one of sodium carbonate, sodium bicarbonate, potassium carbonate, potassium bicarbonate, triethylamine or pyridine as a base are used in an organic solvent.

The compounds of the above formula (I) according to the present invention have a strong herbicidal activity against barnyardgrass, the most troublesome weed and strong safety on paddy rice.

Therefore, the above formula (I) compounds of the present invention are very useful as herbicides to kill or to control barnyardgrass.

New 3,7-dichloro-8-quinolinyoxadiazole derivatives according to the present invention are listed in the following Table 1.

TABLE 1

| Compound No. | R | m.p. (°C.) |
|---|---|---|
| 1 | isopropyl | 191–192 |
| 2 | cyclopropyl | |
| 3 | t-butyl | 215–216 |
| 4 | —HC(Me)(Ph) | 152–160 |
| 5 | —HC(Ph)(Ph) | 198–199 |
| 6 | phenyl | |
| 7 | 2-Cl-phenyl | 214–215 |
| 8 | 3-Cl-phenyl | |
| 9 | 4-Cl-phenyl | 224–225 |
| 10 | 2-Br-phenyl | 213–214 |

TABLE 1-continued
| Compound No. | R | m.p. (°C.) |
|---|---|---|
| 11 | 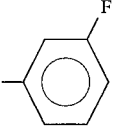 2-F-C6H4 | 224–225 |
| 12 | 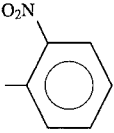 2-O2N-C6H4 | 192–193 |
| 13 | 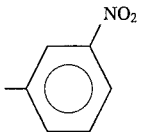 3-NO2-C6H4 | 226–227 |
| 14 | 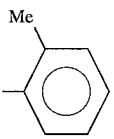 2-Me-C6H4 | |
| 15 | 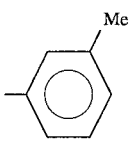 3-Me-C6H4 | |
| 16 | 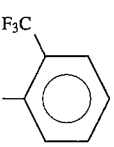 2-CF3-C6H4 | |
| 17 | 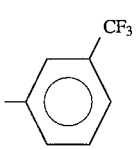 3-CF3-C6H4 | 208–209 |
| 18 | 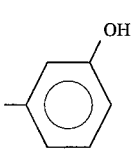 3-OH-C6H4 | 195–196 |
| 19 | 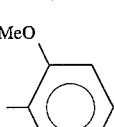 2-MeO-C6H4 | 189–190 |
| 20 | 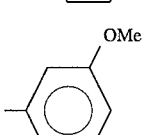 3-MeO-C6H4 | 213–214 |
| 21 | 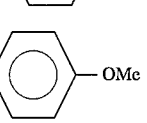 4-MeO-C6H4 | 210–211 |

TABLE 1-continued
| Compound No. | R | m.p. (°C.) |
|---|---|---|
| 22 | 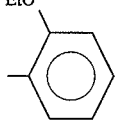 EtO | 184–185 |
| 23 | 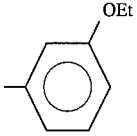 OEt | 179–180 |
| 24 | 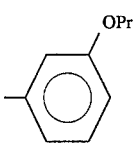 OPr | 202–203 |
| 25 | 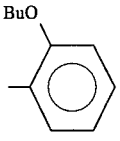 BuO | 199–201 |
| 26 | 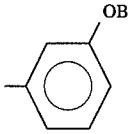 OBu | 182–183 |
| 27 | 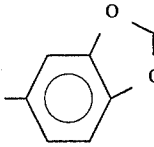 | 209–210 |
| 28 | 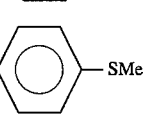 SMe | 220–221 |
| 29 | 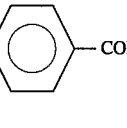 COMe | 200–201 |
| 30 | 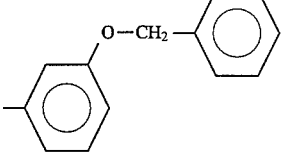 | |
| 31 | 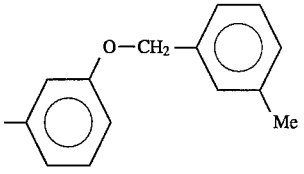 | |

TABLE 1-continued

| Compound No. | R | m.p. (°C.) |
|---|---|---|
| 32 | 3-methylphenyl-O-CH₂-(2-methylphenyl) | |
| 33 | 3-methylphenyl-O-CH₂-(4-chloro-2-methylphenyl) | |
| 34 | 2-methylpyridin-yl | |
| 35 | 3-methylpyridin-yl | |
| 36 | —CH₂—phenyl | 174–175 |
| 37 | —CH₂—(2-chlorophenyl) | |
| 38 | —CH₂—(3-chlorophenyl) | 162–163 |
| 39 | —CH₂—(4-chlorophenyl) | 160–162 |
| 40 | —CH₂—(2-fluorophenyl) | 163–164 |
| 41 | —CH₂—(3-fluorophenyl) | 134–135 |
| 42 | —CH₂—(4-fluorophenyl) | 153–154 |

TABLE 1-continued
| Compound No. | R | m.p. (°C.) |
|---|---|---|
| 43 | 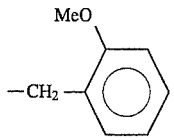 |  |
| 44 | 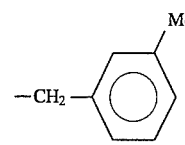 | 172–173 |
| 45 | 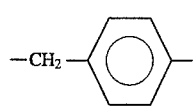 | 166–167 |
| 46 | 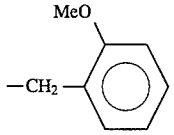 | 162–163 |
| 47 | 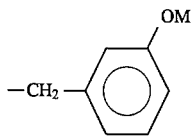 | 124–125 |
| 48 | 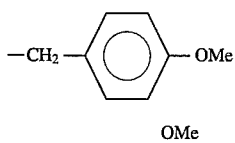 | 110–112 |
| 49 | 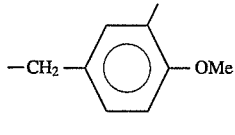 | 190–195 |
| 50 | 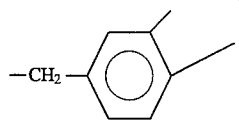 | 168–169 |
| 51 | 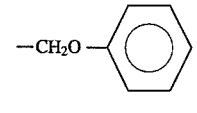 | 187–189 |
| 52 | 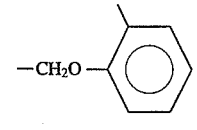 |  |
| 53 | 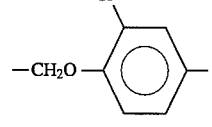 | 173–174 |

TABLE 1-continued
| Compound No. | R | m.p. (°C.) |
|---|---|---|
| 54 | 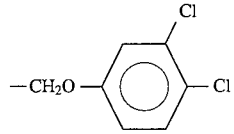 | |
| 55 | 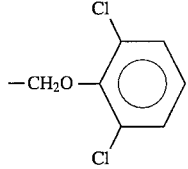 | |
| 56 | 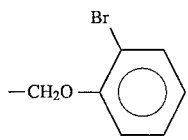 | |
| 57 | 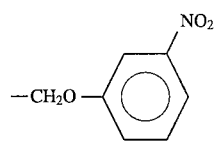 | |
| 58 | 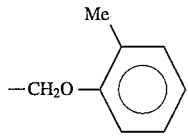 | 189–190 |
| 59 | 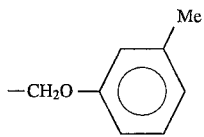 | 189–191 |
| 60 | 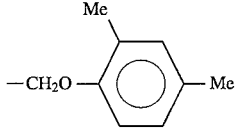 | |
| 61 | 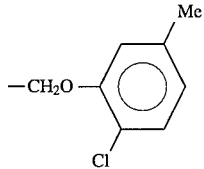 | 162–164 |
| 62 | 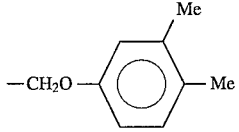 | |
| 63 | 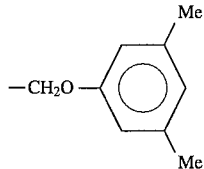 | |

TABLE 1-continued

| Compound No. | R | m.p. (°C.) |
|---|---|---|
| 64 | —CH₂O—(2,6-di-Me-phenyl) | |
| 65 | —CH₂O—(2,4,6-tri-Me-phenyl) | |
| 66 | —CH₂O—(3-Ph-phenyl) | |
| 67 | —CH₂O—(2,4-di-Me-phenyl) | |
| 68 | —CH₂O—(2,3-di-Me-phenyl) | |
| 69 | —CH₂O—(3-Et-phenyl) | |
| 70 | —CH₂O—(2-Et-phenyl) | |
| 71 | —CH₂O—(2,3,6-tri-Me-phenyl) | |
| 72 | —CH₂O—(2,3,4-tri-Me-phenyl) | |

TABLE 1-continued

| Compound No. | R | m.p. (°C.) |
|---|---|---|
| 73 | —CH₂O—(3-i-pr-phenyl) | |
| 74 | —CH₂O—(2-t-Bu-4-Me-phenyl) | |
| 75 | —CH₂O—(2,6-di-t-Bu-4-Me-phenyl) | |
| 76 | —CH₂O—(2,4-di-F-phenyl) | |
| 77 | —CH₂O—(2,3-di-t-Bu-phenyl) | |
| 78 | —CH₂O—(2-t-Bu-phenyl) | |
| 79 | —CH₂O—(2,4-di-t-Bu-phenyl) | |
| 80 | —CH₂O—(4-sec-Bu-phenyl) | |
| 81 | —CH₂O—(2-iso-Bu-phenyl) | |
| 82 | —CH₂O—(2-Cl-4-F-5-NO₂-phenyl) | |

TABLE 1-continued
| Compound No. | R | m.p. (°C.) |
|---|---|---|
| 83 | 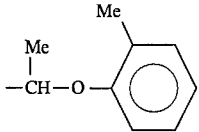 | |
| 84 | 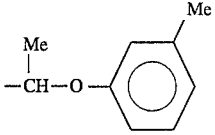 | |
| 85 | 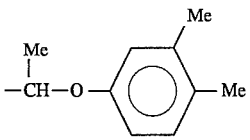 | |
| 86 | 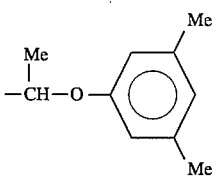 | |
| 87 | 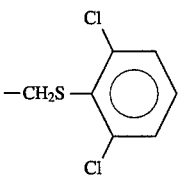 | |
| 88 | 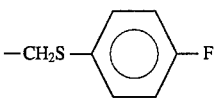 | |
| 89 | 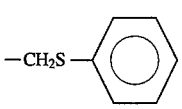 | |
| 90 | 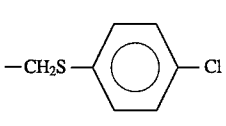 | |
| 91 | 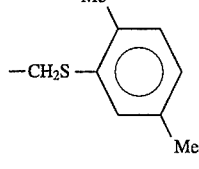 | |
| 92 | 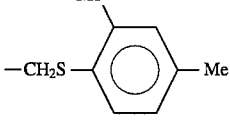 | |
| 93 | 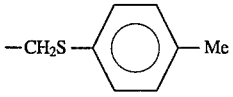 | |

TABLE 1-continued

| Compound No. | R | m.p. (°C.) |
|---|---|---|
| 94 | 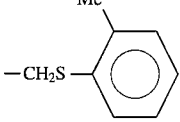 | |

Preparation of the present invention is illustrated by following Examples, but should not be construed to be limited thereto.

EXAMPLE 1

Isopropyl amidoxime (II, R=isopropyl)

To a solution of hydroxylamine hydrochloride (7.0 g, 0.1 mol) and sodium bicarbonate(8.4 g, 0.1 mol) in distilled water(25 ml) was added isobutyronitrile(3.45 g, 50 mmol) in ethanol(50 ml). After refluxing for 16 hours the reaction mixture was concentrated under reduced pressure to afford a crude product. The crude product was extracted with ethanol and concentrated under reduced pressure, and then the desired product(2.3 g, yield=45%) was obtained by silica-gel column chlomatography using a mixture of chloroform and ethanol(19:1→4:1) as a eluent.

EXAMPLE 2

3.7-Dichloro-8-quinolinecarboxylic acid chloride (III)

3,7-Dichloro-8-quinolinecarboxylic acid(20 g, 82 mmol) was added to thionyl chloride(80 ml), and the mixture refluxed for 3 hours and concentrated under reduced pressure to afford the desired product(20.6 g, yield=95.7%) as a light brown solid.

$^1$H NMR(DMSO-$d_6$): δ8.0(dd, 2H), 8.9(dd, 2H)

EXAMPLE 3

3-Isopropyl-5-(3', 7'-dichloro-8'-quinolinyl)-1,2,4-oxadiazole(I, R=isopropyl)

To a solution of isopropyl amidoxime(0.51 g, 5 mmol) in 5 ml of dry pyridine was added 3,7-dichloro-8-quinolinecarboxylic acid chloride(1.3 g, 5 mmol) in 5 ml of dichloromethane. After refluxing for 18 hours, the reaction mixture was concentrated under reduced pressure, diluted with 50 ml of distilled water and then filtered the precipitate to afford a crude product as a solid. Final purification was performed by silica-gel column chromatography using a mixture of chloroform and ethanol(19:1→9:1) as a eluent to afford the desired product(1.17 g, yield=80%) as a light yellow solid.

m.p.: 191°~192° C. $^1$H NMR(DMSO-$d_6$): δ1.1(d, 6H), 2.4(heptet, 1H), 8.0(dd, 2H), 8.85(dd, 2H)

Other compounds of the present invention were prepared by the methods of the Examples given the above. They were characterized by $^1$H NMR spectra and mass spectra which are given in the following Table 2.

$^1$H NMR represents a proton nuclear magnetic resonance spectrum and the solvent used in the measurement is shown in round brackets.

TABLE 2

| Compound No. | $^1$H NMR(DMSO-$d_6$) | Mass Analysis(70eV) |
|---|---|---|
| 1 | 1,1(d, 6H), 2.4(heptet, 1H), 8.0(dd, 2H), 8.85(dd, 2H) | |
| 3 | 1.3(s, 9H), 8.1(dd, 2H), 9.0(dd, 2H) | |
| 4 | 1.4(d, 3H), 3.6(q, 1H), 7.3(m, 5H), 8.1(dd, 2H), 8.95(dd, 2H) | |
| 5 | 5.8(s, 1H), 7.5–8.3(m, 12H), 8.9(dd, 2H) | |
| 10 | 7.0–8.2(m, 6H), 8.8(dd, 2H) | |
| 11 | 7.5–7.85(m, 4H), 8.1(dd, 2H), 8.85(dd, 2H) | 161(22), 224(100), 226(86) 342(14), 360($M^+$, 2) |
| 13 | 7.3–7.4(m, 3H), 8.0(m, 3H), 8.9(dd, 2H) | 197(21), 226(100), 224(100), 369(13), 387($M^+$, 1) |
| 15 | 2.3(s, 3H), 7.3–7.6(m, 3H), 8.0(dd, 2H), 8.9(dd, 2H) | |
| 17 | 7.8–8.3(m, 6H), 8.9(dd, 2H) | |
| 18 | 7.1–7.3(m, 4H), 7.8(d, 2H), 8.5(dd, 2H) | |
| 19 | 3.8(s, 3H), 6.8–7.8(m, 4H), 8.05(dd, 2H), 8.8(dd, 2H) | |
| 20 | | 197(19), 223(100), 225(61), 338(12), 172($M^+$, 8) |
| 22 | 1.3(t, 3H), 4.05(q, 2H), 7.0–7.4(m, 4H), 8.0(dd, 2H), 8.85(dd, 2H) | |
| 23 | 1.3(t, 3H), 4.1(q, 2H), 7.0–7.3(m, 4H), 8.1(dd, 2H), 8.9(dd, 2H) | |
| 25 | 1.0(t, 3H), 1.2–1.8(m, 4H), 4.0(t, 2H), 7.0–8.2(m, 6H), 8.9(dd, 2H) | |
| 26 | 1.0(m, 3H), 1.3–1.6(m, 4H), 4.0(t, 2H), 7.0–7.1(m, 4H), 8.05(dd, 2H), 8.95(dd, 2H) | |
| 27 | 3.9(s, 2H), 7.4–7.5(m, 3H), 8.05(d, 2H), | 224(100), 226(63), 368(17), |

TABLE 2-continued

| Compound No. | ¹H NMR(DMSO-d₆) | Mass Analysis(70eV) |
|---|---|---|
| | 8.85(dd, 2H) | 385(10), 387(M⁺, 8) |
| 30 | 5.0(s, 2H), 6.8–8.2(m, 11H), 8.8(dd, 2H) | |
| 31 | 2.3(s, 3H), 5.1(s, 2H), 6.9–8.2(m, 10H), 8.9(dd, 2H) | |
| 32 | 2.2(s, 3H), 5.1(s, 2H), 6.8–8.2(m, 10H), 8.9(dd, 2H) | |
| 33 | 2.2(s, 3H), 5.2(s, 2H), 7.0–8.3(m, 9H), 8.9(dd, 2H) | |
| 39 | 3.8(s, 2H), 7.1–7.2(m, 4H), 7.8(d, 2H), 8.5(dd, 2H) | |
| 40 | 3.9(s, 2H), 7.0–7.1(m, 4H), 7.8(d, 2H), 8.4(dd, 2H) | |
| 41 | 3.8(s, 2H), 7.15(m, 4H), 7.8(d, 2H), 8.4(dd, 2H) | |
| 42 | 1.95(d, 2H), 6.5(brs, 1H), 6.9–7.3(m, 3H), 7.9(dd, 2H), 8.8(dd, 2H) | |
| 44 | 2.3(s, 3H), 3.5(s, 2H), 7.1(m, 4H), 8.0(dd, 2H), 8.95(dd, 2H) | |
| 45 | 3,3(d, 2H), 7.5–7.8(m, 4H), 8.0(d, 2H), 8.9(dd, 2H) | |
| 46 | 3.3(s, 3H), 3.9(d, 2H), 6.9–7.3(m, 4H), 8.0(dd, 2H), 8.9(dd, 2H) | |
| 47 | 3.4(s, 3H), 3.9(d, 2H), 6.8–7.3(m, 4H), 8.0(dd, 2H), 8.9(dd, 2H) | |
| 48 | 3.8(s, 6H), 6.9–7.3(m, 4H), 8.0(dd, 2H), 8.9(dd, 2H) | |
| 49 | 3.3(s, 6H), 3.8(d, 2H), 6.5(brs, 1H), 6.9–7.0(m, 2H), 8.0(dd, 2H), 8.9(dd, 2H) | |
| 50 | 3.3(d, 2H), 6.0(s, 2H), 6.8–7.0(m, 4H), 8.0(dd, 2H), 8.9(dd, 2H) | |
| 51 | 4.9(s, 2H), 7.1–7.2(m, 5H), 7.9(d, 2H), 8.6(dd, 2H) | 148(51), 224(100), 226(93), 261(4), 354(5), 372(M⁺, 4) |
| 52 | 4.8(s, 2H), 6.9–7.4(m, 4H), 7.9(dd, 2H), 8.9(dd, 2H) | |
| 53 | 4.9(s, 2H), 7.1–7.5(m, 3H), 7.9(d, 2H), 8.6(dd, 2H) | |
| 56 | 4.6(s, 2H), 7.0–8.2(m, 6H), 8.95(dd, 2H) | |
| 57 | 4.9(s, 2H), 7.5–8.5(m, 6H), 9.0(dd, 2H) | |
| 58 | 2.2(s, 3H), 4.8(s, 2H), 6.8–7.2(m, 4H), 7.9(dd, 2H), 8.85(dd, 2H) | |
| 59 | 2.3(s, 3H), 5.2(s, 2H), 6.8–7.2(m, 4H), 8.0(dd, 2H), 8.85(dd, 2H) | |
| 61 | 2.2(s, 3H), 5.2(s, 2H), 6.9–7.2(m, 4H), 8.0(dd, 2H), 8.9(dd, 2H) | |
| 67 | 2.2(s, 3H), 2.4(s, 3H), 4.7(s, 2H), 7.1(s, 2H), 7.25(s, 1H), 7.8(d, 2H) 8.5(d, 2H) | |
| 69 | 1.3(t, 3H), 3.7(q, 2H), 4.9(s, 2H), 7.1(q, 4H), 7.8(d, 2H), 8.6(d, 2H) | |
| 70 | 1.3(t, 3H), 3.7(q, 2H), 4.9(s, 2H), 7.1(q, 4H), 7.8(d, 2H), 8.6(d, 2H) | |
| 72 | 2.15(s, 3H), 2.3(s, 6H), 4.8(s, 2H), 6.8(s, 2H), 7.8(d, 2H), 8.6(d, 2H) | |
| 73 | 0.9(d, 2H), 2.7(m, 1H), 4.75(s, 2H), 7.7(d, 2H), 8.5(d, 2H) | |
| 74 | 1.3(s, 9H), 3.2(s, 3H), 4.9(s, 2H), 7.0–7.4(m, 3H), 7.9(d, 2H), 8.6(d, 2H) | |
| 75 | 1.2(s, 9H), 1.3(s, 9H), 3.25(s, 3H), 4.9(s, 2H), 7.0–7.4(d, 2H), 7.9(d, 2H), 8.6(d, 2H) | |
| 76 | 4.9(s, 2H), 7.0–7.4(m, 3H), 7.9(d, 2H), 8.6(d, 2H) | |
| 77 | 1.3(s, 9H), 3.2(s, 3H), 4.9(s, 2H), 7.0–7.4(m, 3H), 7.9(d, 2H), 8.6(d, 2H) | |
| 78 | 1.3(s, 9H), 4.8(s, 2H), 7.0–7.3(m, 4H), 7.8(d, 2H), 8.6(d, 2H) | |
| 79 | 1.2(s, 9H), 1.35(s, 9H), 4.9(s, 2H), 7.0–7.4(m, 4H), 7.9(d, 2H), 8.6(d, 2H) | |
| 80 | 0.75–0.9(t, 3H), 1.1–1.3(d, 3H), 1.4–1.8(q, 2H), 2.4–2.8(q, 1H), 4.8(s, 2H), 7.0–7.4(m, 4H), 7.9(d, 2H), 8.6(d, 2H) | |
| 81 | 0.75–0.9(t, 3H), 1.15–1.3(d, 3H), 1.4–1.8(q, 2H), 2.4–2.8(q, 1H), 4.85(s, 2H), 7.0–7.4(m, 4H), 7.9(d, 2H), 8.6(d, 2H) | |
| 82 | 4.9(s, 2H), 7.2–7.6(q, 2H), | |

TABLE 2-continued

| Compound No. | ¹H NMR(DMSO-d$_6$) | Mass Analysis(70eV) |
|---|---|---|
| | 7.8(d, 2H), 8.6(d, 2H) | |
| 83 | 1.55(d, J=6.3Hz, 3H), 2.20(s, 3H), 4.75(q, J=6.3Hz, 1H), 6.65–7.20(m, 4H), 7.8–8.2(dd, 2H), 8.8–9.0(dd, 2H) | |
| 84 | 1.50(d, J=6.3Hz, 3H), 2.25(s, 3H), 4.80(q, J=6.3Hz, 1H), 6.70–6.90(m, 4H), 7.8–8.2(dd, 2H), 8.8–9.0(dd, 2H) | |
| 85 | 1.50(d, J=6.3Hz, 3H), 2.15(s, 3H), 2.19(s, 3H), 4.73(q, J=6.3Hz, 1H), 6.65–7.05(m, 3H), 7.8–8.2(dd, 2H), 8.7–9.0(dd, 2H) | |
| 86 | 1.52(d, J=6.3Hz, 3H), 2.22(s, 6H), 4.77(q, J=6.3Hz, 1H), 6.55–6.80(m, 3H), 7.8–8.2(dd, 2H), 8.7–9.0(dd, 2H) | |
| 87 | 3.6(s, 2H), 6.8(s, 1H), 7.1(s, 2H), 7.8(d, 2H), 8.6(d, 2H) | |
| 88 | 3.6(s, 2H), 7.1–7.3(q, 4H), 7.8(d, 2H), 8.6(d, 2H) | |
| 89 | 3.6(s, 2H), 7.1–7.3(m, 5H), 7.8(d, 2H), 8.6(d, 2H) | |
| 90 | 3.6(s, 2H), 7.1–7.4(m, 4H), 7.8(dd, 2H), 8.6(dd, 2H) | |
| 91 | 2.25(s, 6H), 3.65(s, 2H), 6.85–7.35(m, 4H), 7.8–8.2(dd, 2H), 8.6–9.0(dd, 2H) | |
| 92 | 2.15(s, 3H), 2.35(s, 3H), 3.6(s, 2H), 6.8–7.2(m, 3H), 7.8(d, 2H), 8.6(d, 2H) | |
| 93 | 2.3(s, 3H), 3.6(s, 2H), 7.1–7.3(q, 4H), 7.8(d, 2H), 8.6(d, 2H) | |
| 94 | 2.3(s, 3H), 3.65(s, 2H), 7.2–7.4(m, 4H), 7.9(d, 2H), 8.7(d, 2H) | |

The compounds in Table 2 of said formula (I) may be applied for instance in the form of wettable powders, oil suspensions, granules, solutions or dusts.

To prepare the above formulations can be used either solid carder or liquid carrier. As solid carders, inorganic powders such as kaolinite, bentonite, montmorillonite, talc diatomaceous earth, mica, gypsum, calcium carbonate, apatite, synthesized silicon hydroxide hydrate; plant powders such as soy powder, wheat powder, sawdust, tabacco powder, starch powder, crystallized cellulose; polymers such as petroleum resin, vinyl chloride resin, ketone resin; alumina or beeswax etc. can be used.

And as liquid carriers, alcohols such as methanol, ethanol, ethyleneglycol, benzyl alcohol; aromatic hydrocarbons such as toluene, benzene, xylene, methyl naphthalene, halo hydrocarbons such as chloroform, carbon tetrachloride, chlorobenzene; ethers such as dioxane, tetrahydrofuran; ketones such as acetone, methyl ethyl ketone, cyclohexanone; esters such as ethyl acetate, butyl acetate, ethyleneglycol acetate; amides such as dimethyl formamide; nitriles such as acetonitrile; ether alcohols such as ethylene glycol, diethyl ethers or water etc. can be used.

Surfactants can be advantageously employed herein such as various cationic, anionic and nonionic surfactants.

Cationic surfactants include long chain alkylammonium salts such as cetyltrimethylammonium bromide, etc.

Anionic surfactants include alkali metal, alkaline earth metal and ammonium salts of alkylaryl sulfonic acids such as dodecylbenzenesulfonic acid; alkyl sulfonic acids; alkyl sulfuric acids such as laurylsulfuric acid; ligninsulfonic acid; arylsulfonic acids such as naphthalene sulfonic acid or dibutylnaphthalenesulfonic acid; lauryl ether sulfate; fatty alcohol sulfates; fatty acids; salts of sulfated hexadecanols, heptadecanols or octadecanols; salts of sulfated fatty alcohol glycol ethers, etc.

Examples of nonionic surfactants include condensation products of fatty alcohols such as oleyl alcohol or cetyl alcohol; phenols; alkylphenols or caster oil with ethylene oxide or propylene oxide; condensation products of naphthalene or naphthalene sulfonic acids with phenol or formaldehyde, etc.

The content of the compound represented by the above formula (I), while varying depending on the formulations, is usually from 1 to 50% by weight for the wattable powders, the granules or the emulsifiable formulations, and from 20 to 40% by weight for the flowable or the dry flowable formulations.

The application amount of compound represented by the formula (I) is from 60 g to 1000 g/ha, preferably from 60 g to 600 g/ha.

The active herbicidal compounds of this invention may be formulated with insecticides, fungicides, nematocides, plant growth regulators, fertilizers, other herbicides or other agricultural chemicals. The active herbicidal compounds of this invention may be used in combination with other herbicides to increase the herbicidal spectrum and to achieve synergic effects. Examples of useful complementary herbicides include benzothiadiazinone herbicides such as 3-isopropyl-1H-2,1,3-benzothiadiazin-4(3H)one-2,2-dioxide(bentazone); N-(heteroarylaminocarbonyl)benzenesulfonamides such as methyl 2-[3-(4,6-dimethoxypyrimidin-2-yl)ureidosulfonylmethyl]benzoate(Londax), ethyl 5-[3-(4,6-dimethoxypyrimidin-2-yl)ureidosulfonyl]-1-methylpyrazole-4-carboxylate(pyrazosulfuronethyl,NC-311).

The herbicidal activity of compounds of the above formula (I) is performed in greenhouse experiments and some of typical test examples are given below.

(A) Primary screening procedure for barnyardgrass and rice.

A plastic pot having a surface area of 140 cm² was filled with puddled sandy loam soil contained 1.2% organic matter(pH 6.0). Japonica rice seedlings at the 2.0 to 2.5 leaf stage and pregerminated seeds of Japonica rice were transplanted at the depth of 2 cm and seeded at the depth of 0.5 cm, respectively, and seeds of barnyardgrass(*Ecinochloa crus-galli*) were seeded, wherein the pot was watered at the depth of 3 cm just after planting. Two days after, a solution of the test compound in 50% aqueous acetone containing 0.1% Tween 20 was applied into the water. When the test compound was insoluble in the above solvent system, it was formulated as a wettable powder. The concentration of the test compound in solution or wettable powder was varied to give a range of application rates, generally 1.0 kg/ha and submutiples thereof.

Two to three weeks after the application of the herbicide, herbicidal effect on barnyardgrass and phytotoxicity to the paddy rice plant were visually rated by a percentage grading wherein 0 signifies no herbicidal effect or no phytotoxicity and 100 signifies complete kill. The results are shown in Table 3.

(B) Procedure for barnyardgrass stage test

Pots filled with sandy loam soil as described above was sowed subsequently with seeds of barnyardgrass at three different times at the intervals of 5 days and the weeks were allowed to grow up to the 2, 3, and 4 leaf stages of barnyardgrass before the application of a herbicide. Three weeks after herbicidal activity was visually rated. The results are shown in Table 4.

(C) Procedure for rice injury test

This procedure was carried out by the similar methods described above except that seeds of Japonica rice were sowed and allowed to grow up to three different stages of 1, 2 and 3 leaves before the application of a herbicide. Three weeks after phytotoxicity to the paddy rice was visually rated. The results are shown in Table 5.

TABLE 3

| Compound No. | Application rate (kg/ha) | Rice (3 Lf) | Direct seeded rice | Barnyard-grass |
|---|---|---|---|---|
| 1 | 1 | 50 | 70 | 100 |
|  | 0.25 | 30 | 20 | 100 |
|  | 0.06 | 20 | 10 | 100 |
| 3 | 1 | 40 | 40 | 100 |
|  | 0.25 | 10 | 20 | 100 |
|  | 0.06 | 10 | 0 | 100 |
| 4 | 1 | 0 | 90 | 100 |
|  | 0.25 | 0 | 30 | 100 |
|  | 0.06 | 0 | 20 | 100 |
| 8 | 1 | 0 | 0 | 100 |
|  | 0.5 | 0 | 0 | 100 |
|  | 0.25 | 0 | 0 | 100 |
| 11 | 1 | 10 | 30 | 100 |
|  | 0.5 | 0 | 10 | 100 |
|  | 0.25 | 0 | 0 | 90 |
|  | 0.125 | 0 | 0 | 90 |
| 13 | 1 | 10 | 30 | 100 |
|  | 0.5 | 10 | 30 | 100 |

TABLE 3-continued

| Compound No. | Application rate (kg/ha) | Rice (3 Lf) | Direct seeded rice | Barnyard-grass |
|---|---|---|---|---|
|  | 0.25 | 0 | 20 | 100 |
|  | 0.125 | 0 | 0 | 100 |
|  | 0.06 | 0 | 0 | 80 |
| 15 | 1 | 30 | 20 | 100 |
|  | 0.25 | 10 | 0 | 100 |
|  | 0.06 | 10 | 0 | 90 |
| 17 | 1 | 10 | 40 | 100 |
|  | 0.5 | 0 | 0 | 100 |
|  | 0.25 | 0 | 0 | 100 |
|  | 0.125 | 0 | 0 | 90 |
| 25 | 1 | 0 | 20 | 100 |
|  | 0.25 | 0 | 0 | 100 |
|  | 0.06 | 0 | 0 | 100 |
| 27 | 1 | 10 | 10 | 100 |
|  | 0.5 | 0 | 0 | 100 |
|  | 0.25 | 0 | 0 | 90 |
| 51 | 1 | 20 | 70 | 100 |
|  | 0.5 | 20 | 70 | 100 |
|  | 0.25 | 0 | 50 | 100 |
|  | 0.125 | 0 | 20 | 100 |
|  | 0.06 | 0 | 0 | 90 |
| 58 | 1 | 10 | 40 | 100 |
|  | 0.5 | 0 | 10 | 100 |
|  | 0.25 | 0 | 0 | 100 |
|  | 0.125 | 0 | 0 | 100 |
| 59 | 1 | 0 | 20 | 100 |
|  | 0.5 | 0 | 0 | 100 |
|  | 0.25 | 0 | 0 | 100 |
|  | 0.125 | 0 | 0 | 100 |
| 66 | 1 | 0 | 0 | 80 |
| 70 | 1 | 0 | 20 | 100 |
|  | 0.25 | 0 | 0 | 100 |
|  | 0.062 | 0 | 0 | 95 |
| 71 | 1 | 0 | 30 | 100 |
|  | 0.25 | 0 | 30 | 100 |
|  | 0.062 | 0 | 0 | 100 |
| 72 | 1 | 0 | 30 | 100 |
|  | 0.25 | 0 | 20 | 100 |
|  | 0.062 | 0 | 0 | 100 |
| 73 | 1 | 0 | 40 | 100 |
|  | 0.25 | 0 | 20 | 100 |
|  | 0.062 | 0 | 0 | 100 |
| 75 | 1 | 0 | 40 | 100 |
|  | 0.25 | 0 | 10 | 100 |
|  | 0.062 | 0 | 0 | 95 |
| 78 | 1 | 10 | 20 | 100 |
|  | 0.25 | 0 | 0 | 100 |
|  | 0.062 | 0 | 0 | 90 |
| 79 | 1 | 10 | 70 | 100 |
|  | 0.25 | 0 | 0 | 100 |
|  | 0.062 | 0 | 0 | 90 |
| 83 | 1 | 20 | 20 | 100 |
|  | 0.25 | 0 | 0 | 100 |
|  | 0.062 | 0 | 0 | 100 |
| 86 | 1 | 20 | 40 | 100 |
|  | 0.25 | 0 | 10 | 100 |
|  | 0.062 | 0 | 0 | 100 |
| 94 | 0.05 | 10 | 0 | 100 |
|  | 0.0125 | 0 | 0 | 100 |

TABLE 4

| Compound No. | Application rate (g/ha) | Barnyardgrass, Percentage control, % | | |
|---|---|---|---|---|
|  |  | 2 LS | 3 LS | 4 LS |
| I-c | 200 | 100 | 100 | 100 |
|  | 100 | 100 | 90 | 80 |
|  | 50 | 90 | 85 | 65 |
| I-d | 200 | 100 | 100 | 95 |

TABLE 4-continued

| Compound No. | Application rate (g/ha) | Barnyardgrass, Percentage control, % | | |
|---|---|---|---|---|
| | | 2 LS | 3 LS | 4 LS |
| | 100 | 100 | 95 | 90 |
| | 50 | 95 | 80 | 60 |
| (C) | 200 | 100 | 100 | 100 |
| | 100 | 100 | 100 | 95 |
| | 50 | 100 | 90 | 65 |

TABLE 5

| Compound No. | Rate (g/ha) | Direct seeded rice, Percentage control, % | | | |
|---|---|---|---|---|---|
| | | 2 DAS | 1 LS | 2 LS | 3 LS |
| I-c | 800 | 20 | 0 | 0 | 0 |
| | 400 | 0 | 0 | 0 | 0 |
| | 200 | 0 | 0 | 0 | 0 |
| | 100 | 0 | 0 | 0 | 0 |
| I-d | 800 | 30 | 10 | 0 | 0 |
| | 400 | 0 | 0 | 0 | 0 |
| | 200 | 0 | 0 | 0 | 0 |
| | 100 | 0 | 0 | 0 | 0 |
| (C) | 800 | 70 | 60 | 40 | 20 |
| | 400 | 50 | 40 | 30 | 20 |
| | 200 | 20 | 10 | 10 | 10 |
| | 100 | 0 | 0 | 0 | 0 |

What is claimed is:

1. A compound of quinolinyloxadiazole derivatives of the following formula (I)

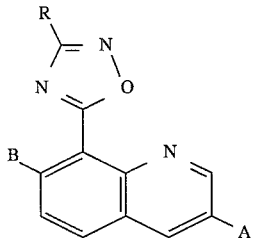

wherein,

A and B are selected from the group consisting of hydrogen, halogen and $C_1$–$C_4$ lower alkyl; and R is $C_3$–$C_4$ alkyl or $C_3$–$C_6$ cycloalkyl, or R is phenyl, benzyl, phenoxyalkyl, phenylthioalkyl, pyridyl, thienyl, or furanyl which are unsubstituted, or are substituted with 1–3 substituents.

2. The compound corresponding to claim 1, wherein the aromatic ring of phenyl, benzyl, phenoxyalkyl or phenylthioalkyl is optionally substituted with 1–3 substituents selected from the group consisting of chloro, bromo, fluoro, nitro, methyl, hydroxy, trifluoromethyl, $C_1$–$C_4$ alkoxy, methylenedioxy, methylthio, acetyl, phenyl and benzyloxy.

3. The compound corresponding to claim 1, wherein R is selected from the group of the following formulas:

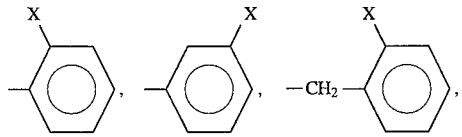

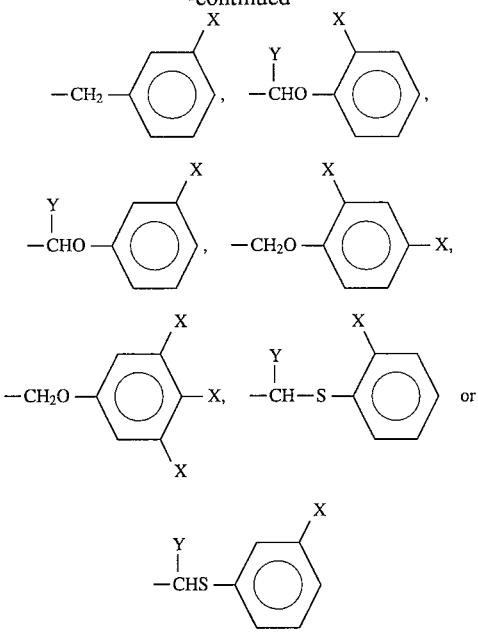

wherein,

X is independently selected from $C_1$–$C_4$ alkyl, $C_1$–$C_4$ alkoxy, chloro, fluoro, trifluoromethyl or nitro; and Y is hydrogen or methyl.

4. The compound corresponding to the claim 1, wherein the above formula (I) is the following formula (I-a):

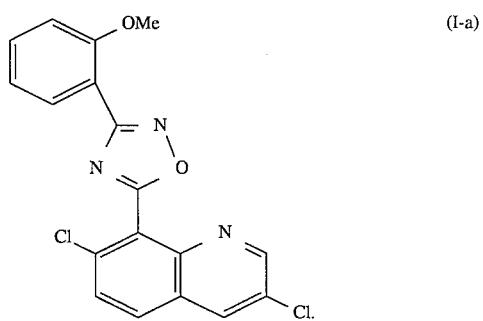

5. The compound corresponding to the claim 1, wherein the above formula (I) is the following formula (I-b):

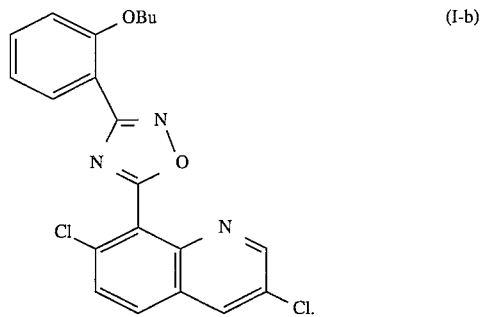

6. The compound corresponding to the claim 1, wherein the above formula (I) is the following formula (I-c):

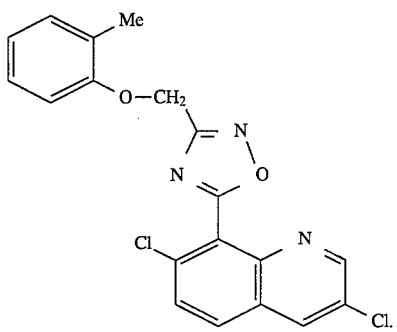
(I-c)

7. The compound corresponding to the claim 1, wherein the above formula (I) is the following formula (I-d):

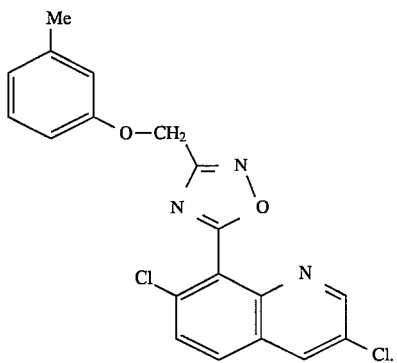
(I-d)

8. The compound corresponding to the claim 1, wherein the above formula (I) is the following formula (I-e):

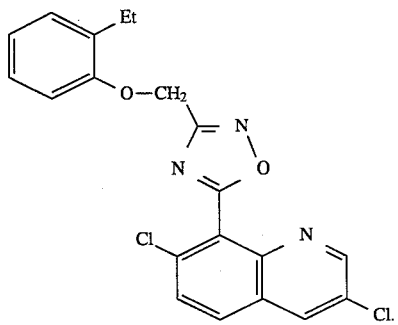
(I-e)

9. The compound corresponding to the claim 1, wherein the above formula (I) is the following formula (I-f):

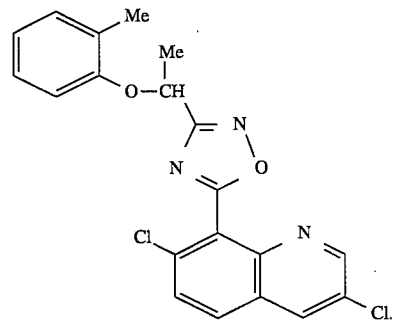
(I-f)

10. The compound corresponding to the claim 1, wherein the above formula (I) is the following formula (I-g):

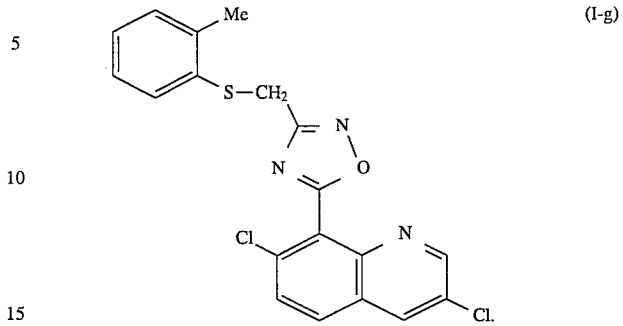
(I-g)

11. A herbicidal composition which comprises a suitable carrier in admixture with a herbicidally effective amount of the compound of formula (I) as claimed in claim 1 as an active ingredient.

12. A method for using quinolinyloxadiazole derivatives characterized by applying an effective amount of the composition of claim 11 to undesired plants in order to kill them or to control their growth.

13. A process for preparing a compound of the formula (I),

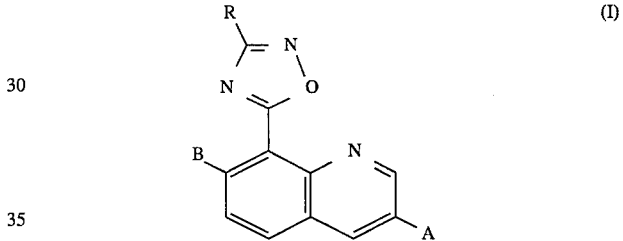
(I)

wherein,

A and B are selected from the group consisting of hydrogen, halogen and $C_1$–$C_4$ lower alkyl; and R is $C_3$–$C_4$ alkyl or $C_3$–$C_6$ cycloalkyl, or R is phenyl, benzyl, phenoxyalkyl, phenylthioalkyl, pyridyl, thienyl, or furanyl which are unsubstituted, or are substituted with 1–3 substituents; characterized by reacting the compound of the following formula (II) with formula (III) in the presence of a base, wherein the base is sodium carbonate, potassium carbonate, triethylamine or pyridine, and of an organic solvent

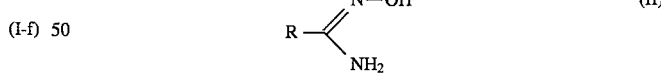
(II)

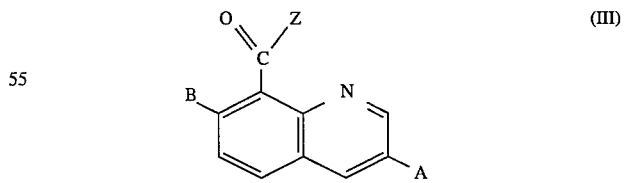
(III)

wherein R, A and B are defined as the above formula (I).

* * * * *